United States Patent [19]

Kamerling

[11] Patent Number: 4,950,290
[45] Date of Patent: Aug. 21, 1990

[54] POSTERIOR CHAMBER INTRAOCULAR LENS

[76] Inventor: William Kamerling, 423 W. Clements Bridge Rd., Barrington, N.J. 08007

[21] Appl. No.: 308,339

[22] Filed: Feb. 9, 1989

[51] Int. Cl.$^5$ .............................................. A61F 2/16
[52] U.S. Cl. ...................................................... 623/6
[58] Field of Search .......................................... 623/6

[56] References Cited

U.S. PATENT DOCUMENTS

| 4,494,254 | 1/1985 | Lopez | 623/6 |
| 4,601,721 | 7/1986 | Kamerling | 623/6 |
| 4,880,427 | 11/1989 | Anis | 623/6 |

FOREIGN PATENT DOCUMENTS

| 8500527 | 1/1986 | Netherlands | 623/6 |
| 0667206 | 6/1979 | U.S.S.R. | 623/6 |

OTHER PUBLICATIONS

Cilco Lens Style Sheet, SK-4 Lens, May 1983.
S. O. Hansen, "Posterior Capsular Opacification and Intraocular Lens Decentration", Journal of Cataract and Refractive Surgery, vol. 14, No. 6, pp. 605-623 (Nov. 1988).
"Animal Studies Back Search for Optimal IOL", Ocular Surgery News, vol. 6, No. 23 (Dec. 1, 1988).

Primary Examiner—Ronald Frinks
Attorney, Agent, or Firm—Panitch Schwarze Jacobs & Nadel

[57] ABSTRACT

A one-piece, polymethylmethacrylate (PMMA) posterior chamber intraocular lens (IOL) for reducing posterior capsular opacification (PCO) and optic decentration includes a biconvex optic disc and a single, flexible, generally circular-shaped loop which extends around the periphery of the disc. The loop is radially compressible, i.e., tightens like a spring coil to achieve substantially 360° contact with the peripheral zone of the posterior capsule with the optic disc centered substantially on the visual axis.

9 Claims, 2 Drawing Sheets

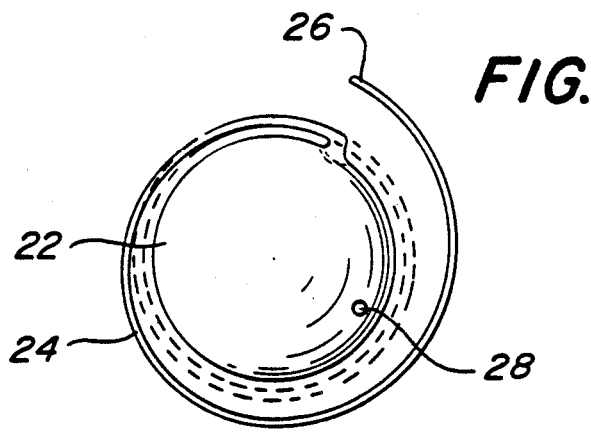
FIG. 2A
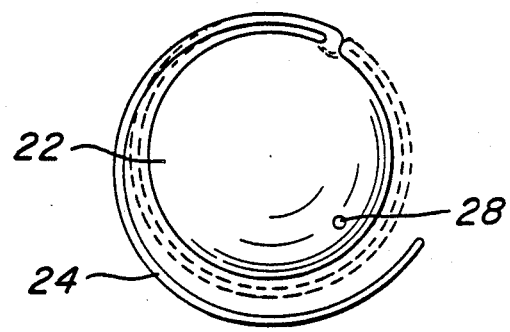
FIG. 2B
FIG. 3
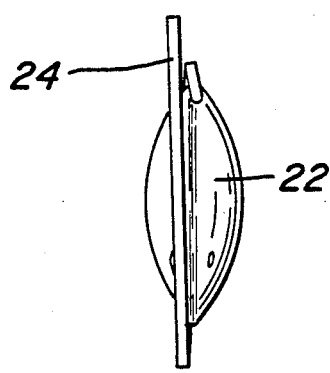
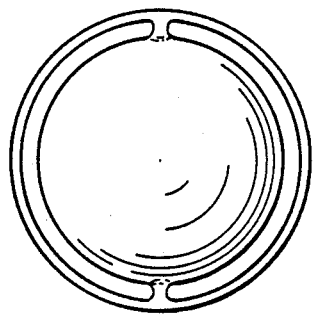
FIG. 5
PRIOR ART

POSTERIOR CHAMBER INTRAOCULAR LENS

FIELD OF THE INVENTION

The invention relates to the field of intraocular lens implants and, in particular, a posterior chamber intraocular lens.

BACKGROUND OF THE INVENTION

Posterior capsular opacification (PCO) and optic decentration are two of the most common complications of modern cataract surgery and intraocular lens (IOL) implantation. The most common cause of PCO is believed to relate to the proliferation and migration of retained lens epithelial cells and their derivatives into the visual axis. The presence of optic components such as positioning holes or optic edges within the pupillary aperture, arising from lens decentration, can cause occupationally debilitating visual aberrations.

Animal studies have shown that the following features having a significant statistical impact on reducing PCO for capsular fixated IOLs: (1) one-piece, all polymethylmethacrylate (PMMA) IOL, (2) biconvex or posterior convex optic design, and (3) angulated loops. S. O. Hansen, Posterior Capsular Opacification And Intraocular Lens Decentration, *Journal Of Cataract And Refractive Surgery* Vol. 14, No. 6, pp. 605-623 (November 1988). Also, the most consistent centration is apparently obtained using one-piece, PMMA IOLs. Optic design (shape and configuration of the optic disc) apparently does not affect lens centration but is significantly related to PCO.

It has been shown that a biconvex optic design and 10° angulated loops, for a one-piece, PMMA posterior chamber IOL, produce the lowest PCO among various optic designs. Hansen, supra. IOLs having a laser ridge optic, meniscus optic (posterior-concave), plano-convex optic (posterior convex or reverse optic) and biconvex optic apparently reduce PCO by inhibiting or minimizing migration of proliferating lens epithelial cells into the visual axis by creating a barrier effect. The barrier effect is best achieved when there is a gentle, taut radial stretch on the capsular sac. PMMA loops apparently have better retention of structural memory and therefore increase the radial stretch of the equatorial capsule that places the capsule under tension and increases the contact of the optic disc with the posterior capsule. This may explain why one-piece, PMMA IOLs have been found to lower PCO irrespective of optic design.

In recent animal studies, a prototype compressible disc IOL (CDIOL) (1) made of onepiece, PMMA, (2) including a biconvex optic, and (3) including an outer fixation ring angled at 10° from the optic, was found to effectively reduce PCO. Hansen, supra. The CDIOL is also described in "Animal Studies Back Search For 'Optimal IOL'", *Ocular Surgery News,* Vol. 6, No. 23 (Dec. 1, 1988). The prototype CDIOL is fabricated from a disc-shaped sheet of solid PMMA. Using a computerized lathe-cutting technique, the lens is fashioned to a biconvex optic disc attached by two connecting bars to an outer fixation ring. The ring has no free end. The lens has a single positioning hole close to the ring to facilitate placement of the superior or twelve o' clock portion of the lens.

Since the outer fixation ring of the CDIOL is coupled to the optic disc by two connecting bars angled at 10° with respect to the disc, the outer fixation ring is situated in a plane anterior to the optic disc. It is believed that the CDIOL effectively reduces PCO by creating a radial stretch of the posterior capsule which is induced by (1) the outer fixation ring which extends 360° around the disc, (2) the angulation of the connecting bars, and (3) the biconvex optic disc. These structural features are believed to maintain the posterior capsule taut while pushing the optic firmly against the posterior capsule, thus providing a mechanical barrier against cell proliferation. Hansen, supra. It is recognized in Hansen, supra, that an IOL with broad circular loop design and angulation, such as the CDIOL or a long C-loop lens in a one-piece design, may prove to further inhibit PCO and decentration upon further study.

SUMMARY OF THE INVENTION

A poster chamber intraocular lens (IOL) for reducing posterior chamber opacification (PCO) and decentration comprises an optic disc and a single, flexible, substantially circular-shaped loop having an end connected to the disc and another end which is free. The loop extends around the periphery of the disc while being spaced radially from the disc. The loop is radially compressible from its original shape to permit insertion of the IOL through a limbal incision into the posterior capsular sac such that the optic disc is centered substantially on the visual axis and the loop is in substantially 360° contact with the peripheral zone of the posterior capsule. A symmetrical, radial stretch is therefore exerted on the posterior capsule so as to keep the capsule taut. This provides a mechanical barrier against cell proliferation.

For the purpose of illustrating the invention, there is shown in the drawings forms which are presently preferred; it being understood, however, that this invention is not limited to the precise arrangements and instrumentalities shown.

BRIEF DESCRIPTION OF THE DRAWINGS

FIG. 2A is a front plan view of the IOL wherein the loop originally extends substantially 360°. around the periphery of the disc so that, upon radial compression, the loop extends substantially more than 360° around the disc.

FIG. 2B is a front plan view of the IOL wherein the loop originally extends less than 360° around the periphery of the disc so that, upon radial compression, the loop extends substantially 360° around the disc.

FIG. 3 is a side view of the IOL shown in FIG. 2A.

FIG. 5 is a diagrammatic representation of the prior art CDIOL.

DETAILED DESCRIPTION OF THE PREFERRED EMBODIMENTS

Figure 1:
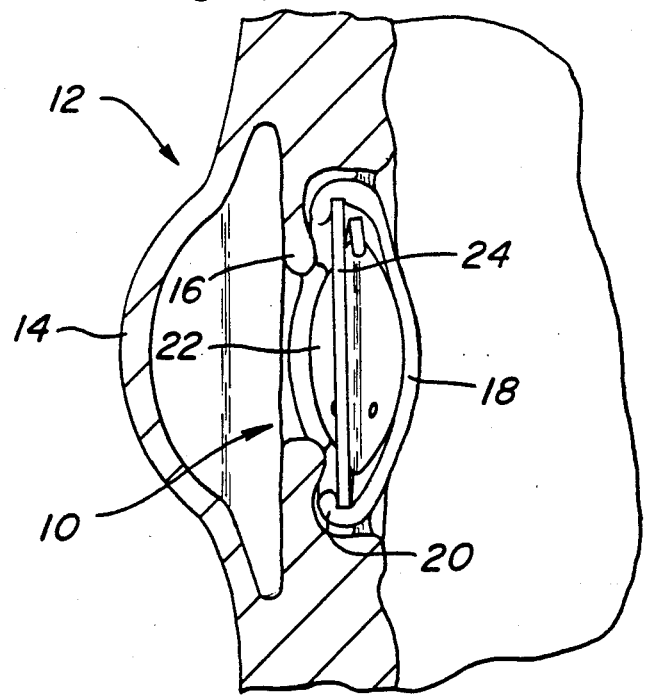
FIG. 1 is a sectional view through an eye showing the posterior chamber IOL in accordance with the present invention implanted in the capsular sac.

Referring to the drawings, wherein like numerals indicate like elements, there is shown in FIG. 1 a posterior chamber IOL in accordance with the present invention designated generally as 10 and implanted in the posterior chamber (capsular sac) of an eye. As is well-known, the eye 12 includes a cornea 14 behind which is located an iris 16 having a centrally disposed opening. Between the iris 16 and a posterior capsule 18 there is provided the posterior chamber. The capsule 18 has an anterior flap 20 which defines a capsular sac within which the IOL can be implanted.

The IOL 10 includes an optic disc 22. Optic disc 22 is preferably plano-convex (posterior convex or reverse optic) or biconvex. A single, flexible, circular-shaped loop 24 is connected in one-piece to the optic disc 22. Thus, the IOL 10 is a one-piece construction. Preferably, the IOL (disc and loop) is made of PMMA.

As shown in FIGS. 2A and 2B, one end of the loop 24 is connected to the optic disc 22, and the other end 26 of the loop is free. Loop 24 extends around the periphery of the optic disc 22 and is radially compressible, similar to the tightening of a spring coil, from its original shape (shown in solid lines) the shape shown in phantom, to permit insertion of the IOL through a limbal incision into the posterior capsular sac. A dialing hole 28 is provided at the ten o' clock position (disc relative to surgeon) to aid centration. As shown in FIG. 3, the loop 24 is preferably angled approximately 8–10° with respect to the optic disc.

Figure 4:
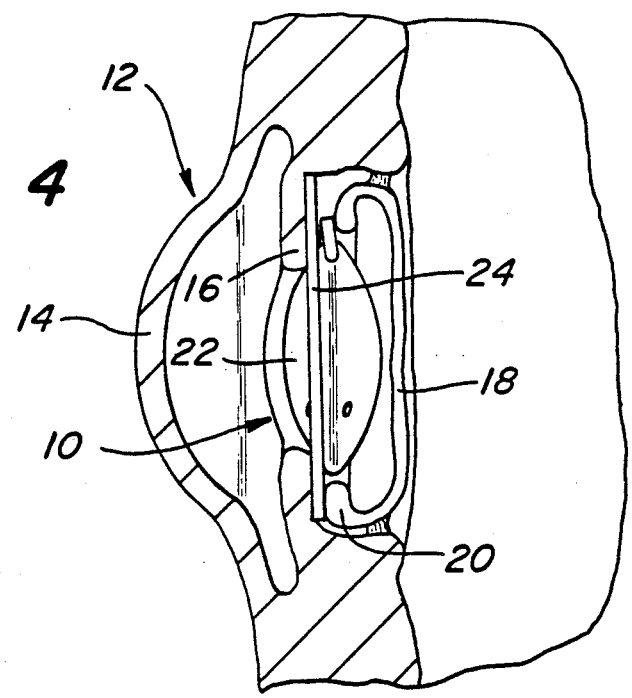
FIG. 4 is a view similar to FIG. 1, but with the IOL implanted in the ciliary sulcus.

In FIG. 1, the IOL 10 is shown fixated in the capsular sac. In FIG. 4, the IOL is shown fixated in the ciliary sulcus. Although either type of fixation is achievable using the IOL, fixation in the capsular sac is preferred to reduce PCO and decentration.

The length and spacing of the loop 24 from the periphery of the optic disc 22 is chosen so that the loop experiences a radial compression, similar to the tightening of a spring coil, when the IOL is fixated in the capsular sac (or ciliary sulcus). The loop will experience slightly less radial compression if the IOL is fixated in the ciliary sulcus since the ciliary sulcus is larger in diameter than the capsular sac. In both cases, loop 24 is shaped and arranged with respect to the optic disc 22 such that when the loop experiences radial compression the optic disc is centered substantially on the visual axis of the eye and the loop is in substantially 360° contact with the peripheral zone of the posterior capsule (or ciliary sulcus).

By way of example, in its original shape, the loop is generally circular in shape having a diameter of approximately 12–13.5 millimeters. The diameter of the optic disc 22 is approximately 6.5–7 millimeters. The average diameter of the capsular sac is 9–10 millimeters, and the average diameter of the ciliary sulcus is 11.5–12millimeters. When the IOL is implanted in the capsular sac, the loop experiences radial compression while closing on itself, tightening like a spring coil. When compressed, the loop 24 exerts a symmetrical, radial stretch on the posterior capsule. This, in combination with the loop angulation and biconvex shape of the optic disc, maintains the posterior capsule taut and pushes the optic disc against the capsule thereby providing a mechanical barrier against cell proliferation. Although a biconvex shape is preferred for the optic disc 22, other shapes such as posterior convex are also acceptable.

For ease of a comparison, a diagrammatic representation of the prior art CDIOL, including a biconvex optic disc 30, flexible loop 32 and connecting bars 34, 36, is shown in FIG. 5. Since loop 32 has no free end, it is incapable of radial compression in the manner of loops 24, 24', of the present invention, i.e., loop 32 cannot close on itself or tighten like a spring coil to fixate the IOL in the capsular sac (or ciliary sulcus).

The present invention may be embodied in other specific forms without departing from the spirit or essential attributes thereof and, accordingly, reference should be made to the appended claims, rather than to the foregoing specification, as indicating the scope of the invention.

I claim:

1. Posterior chamber intraocular lens (IOL) for reducing posterior chamber opacification (PCO), comprising:
   an optic disc,
   a single, flexible, substantially helically shaped loop having a first end generally tangentially connected to the disc and a second end which is free, the loop not being connected to the optic disc other than at said first end,
   the loop extending helically around the periphery of the disc for at least 270° from the first loop end at an angle of 8–10° with respect to the disc while being spaced radially outwardly therefrom at a distance which varies from a minimum proximate the first loop end to a maximum at the second loop end,
   said flexible loop being radially inwardly compressible from its original shape to a generally circular shape with the spacing between the disc and the second loop end generally corresponding to said minimum spacing and the loop extending 360° or slightly less than 360° from the first loop end to provide an overall IOL diameter which is of a size to permit insertion of the IOL through a limbal incision into the posterior capsular sac, the shape and linear length of the loop, the original spacing of the loop from the disc, and the overall original diameter of the IOL being such that when inserted into the capsular sac, the loop expands outwardly and the IOL becomes generally circular, the optic disc is centered substantially on the visual axis and the loop extends radially outwardly from the disc and is in substantially 360° contact with the peripheral zone of the posterior capsule so as to symmetrically and radially stretch the posterior capsule and to maintain uniform contact between the optic disc and the posterior capsule, the length and spacing of the loop being such that if the IOL is inserted into the ciliary sulcus, the loop expands outwardly from the optic disc to maintain uniform contact with the ciliary sulcus to center and stabilize the optic disc.

2. Posterior chamber IOL according to claim 1 wherein said optic disc is posterior convex.

3. Posterior chamber IOL according to claim 2 wherein said optic disc is biconvex.

4. Posterior chamber IOL according to claim 1 wherein said optic disc and loop are a one-piece construction.

5. Posterior chamber IOL according to claim 4 wherein said one-piece construction is made of PMMA.

6. Posterior chamber IOL according to claim 1 wherein the diameter of the second end of said loop in its original shape is 12–13.5 millimeters.

7. Posterior chamber IOL according to claim 1 wherein the diameter of said optic disc is 6.5–7millimeters.

8. Posterior chamber IOL according to claim 1 wherein said optic disc is provided with a dialing hole.

9. Method of implanting an intraocular lens (IOL) in the posterior chamber of the eye, comprising:
   providing an IOL comprising an optic disc, a single, flexible, substantially helically shaped loop having a first end generally tangentially connected to the disc and a second end which is free, the loop not being connected to the optic disc other than at said first end, the loop extending helically for at least 270° from the first loop end around the periphery of the disc at an angle of 8-10° with respect to the disc while being spaced radially outwardly therefrom at a distance which varies from a minimum proximate the first loop and to a maximum at the second loop end, said flexible loop being radially compressible from its original shape, to a generally circular shape with the spacing between the disc and the second loop end generally corresponding to said minimum spacing and the loop extending 360° or slightly less than 360° from the first loop end to provide an overall IOL diameter which is of a size to permit insertion of the IOL through a limbal incision into the posterior capsular sac, forming a limbal incision and inserting the IOL through the limbal incision into the posterior capsular sac of the eye, the shape and linear length of the loop, the original spacing of the loop from the disc, and the overall original diameter of the IOL being such that when inserted into the capsular sac, the loop expands outwardly and the IOL becomes generally circular, the optic disc is centered substantially on the visual axis and the loop extends radially outwardly from the disc and is in substantially 360° contact with the peripheral zone of the posterior capsule so as to symmetrically and radially stretch the posterior capsule and to maintain uniform contact between the optic disc and the posterior capsule, the length and spacing of the loop being such that if the IOL is inserted into the ciliary sulcus, the loop expands outwardly from the optic disc to maintain uniform contact with the ciliary sulcus to center and stabilize the optic disc.

* * * * *